US007037520B2

(12) United States Patent
Smyth Templeton (10) Patent No.: US 7,037,520 B2
(45) Date of Patent: May 2, 2006

(54) REVERSIBLE MASKING OF LIPOSOMAL COMPLEXES FOR TARGETED DELIVERY

(75) Inventor: Nancy Smyth Templeton, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 375 days.

(21) Appl. No.: 10/393,101

(22) Filed: Mar. 20, 2003

(65) Prior Publication Data

US 2003/0180950 A1 Sep. 25, 2003

Related U.S. Application Data

(60) Provisional application No. 60/366,764, filed on Mar. 22, 2002.

(51) Int. Cl.
C12N 15/87 (2006.01)
A61K 9/127 (2006.01)

(52) U.S. Cl. ...................... 424/450; 435/458
(58) Field of Classification Search ................ None
See application file for complete search history.

(56) References Cited

U.S. PATENT DOCUMENTS

| 5,846,951 A | * | 12/1998 | Gregoriadis | .................. | 514/54 |
| 5,945,400 A | | 8/1999 | Scherman et al. | ............ | 514/13 |
| 5,990,089 A | * | 11/1999 | Szoka et al. | .................. | 514/44 |
| 6,096,335 A | | 8/2000 | Thierry | ....................... | 424/450 |

FOREIGN PATENT DOCUMENTS

WO   WO 98/07408   8/1997

OTHER PUBLICATIONS

Smyth Templeton N. 2002. Liposomal delivery of nucleic acids in vivo. DNA and Cell Biol. vol. 21(12) pp. 857-867.*
Choi, Y.H., Liu, F., Kim, J. Choi, Y.K., Park, J.S., Kim, S.W. (1998): Polyethylene glycol-grafted poly-L-lysine as polymeric gene carrier. J. of Controlled Release 54: 39-48.
Behr J-P, Demeneix B, Loeffler JP, Perez-Mutul, J (1989): Efficient gene transfer into mammalian primary endocrine cells with lipopolyamine-coated DNA. Proc Natl Acad Sci USA 86:6982-6986.

Chen, J., Gamou, S., Takayanagi, A., Ohtake, Y., Ohtsubo, M., and Shimizu, N. (1998) Targeted in vivo delivery of therapeutic gene into experimental squamous cell carcinomas using anti-epidermal growth factor receptor antibody: immunogene approach. Human Gene Therapy 9:2673-2681.
Felgner JH, Kumar R, Sridhar CN, Wheeler, CJ, Tsai YJ, Border R, Ramsey,P, Martin, M, and Felgner,P.L. (1994): Enhanced gene delivery and mechanism studies with a novel series of cationic lipid formulations. J Biol Chem 269:2550-2561.
Felgner PL, Gadek TR, Holm M, Roman R, Chan HW, Wenz M, Northrop, JP, Ringold, GM, and Danielsen, M. (1987): Lipofection: a highly efficient lipid-mediated DNA transfection procedure. Proc Natl Acad Sci USA 84:7413-7417.
Felgner PL, and Ringold GM (1989): Cationic liposome-mediated transfection. Nature 337:387-388.
Finsinger D, Remy J-S, Erbacher P, Koch C, Plank C (2000): Protective copolymers by nonviral gene vectors: synthesis, vector characterization and application in gene delivery. Gene Therapy 7:1183-1192.
Gabizon A, Catane R, Uziely B, Kaufman B, Safra T, Cohen R, Martin F, Huang A., Barenholz Y (1994): Prolonged circulation time and enhanced accumulation in malignant exudates of doxorubicin encapsulated in polyethylene-glycol coated liposomes. Cancer Res 54:987-992.
Gordon KB, Tajuddin A, Guitart J, Kuzel TM, Eramo LR, VonRoenn, J (1995): Hand-foot syndrome associated with liposome-encapsulated doxorubicin therapy. Cancer 75:2169-2173.
Gustafsson J, Arvidson G, Karlsson G, Almgren, M (1995): Complexes between cationic liposomes and DNA visualized by cryo-TEM. Biochim Biophys Acta 1235:305-312.
Leventis R, Silvius JR (1990): Interactions of mammalian cells with lipid dispersions containing novel metabolizable cationic amphiphiles. Biochim Biophys Acta 1023:124-132.

(Continued)

*Primary Examiner*—David Guzo
*Assistant Examiner*—Laura McGillem
(74) *Attorney, Agent, or Firm*—Elizabeth R. Hall (57) ABSTRACT

The present invention is a composition and process for avoiding non-specific uptake of targeted liposomal complexes in the lung and other highly vascular issues. The reversible masking of liposomal complexes allows increased delivery of nucleic acid molecules to target cells or tissues.

24 Claims, 6 Drawing Sheets

OTHER PUBLICATIONS

Liu Y, Liggitt D, Zhong W, Guanhuan T, Gaensler K, Debs R (1995): Cationic liposome-mediated intravenous gene delivery. J Biol Chem 270:24864-24870.

Loeffler JP, Behr J-P (1993): Gene transfer into primary and established mammalian cell lines with lipopolyamine-coated DNA. Methods Enzymol 217:599-618.

Ogris M, Brunner S, Schuller S, Kircheis R, and Wagner E.(1999) PEGylated DNA/transferrin-PEI complexes: reduced interaction with blood components, extended circulation in blood and potential for systemic gene delivery. Gene Therapy 6:595-605.

PapahadjopoulosD, Allen TM, Gabizon A, Mayhew E, Matthay K, Huang S K, Lee K, Woodle MC, Lasic DD, Redemann C, Martin FJ (1991): Sterically stabilized liposomes: improvements in pharmacokinetics and antitumor therapeutic efficacy. Proc Natl Acad Sci USA 88:11460-11464.

Pinnaduwage P, Huang L (1989): The role of protein-linked oligosaccharide in the bilayer stabilization activity of glycophorin A for dioleoylphosphatidylethanolamineliposomes. Biochim Biophys Acta 986:106-114.

Ramesh R, Saeki T, Templeton NS, Ji L, Stephens LC, Ito I, Wilson DR, Wu Z, Branch CD, Minna JD, Roth, JA (2001): Successful treatment of primary and disseminated human lung cancers by systemic delivery of tumor suppressor genes using an improved liposome vector. Molecular Therapy 3:337-350.

Rose JK, Buonocore L, Whitt MA (1991): A new cationic liposome reagent mediating nearly quantitative transfection of animal cells. Biotechniques 10:520-525.

Senior J, Delgado C, Fisher D, Tilcock C, Gregoriadis G (1991): Influence of surface hydrophilicity of liposomes on their interaction with plasma protein and clearance from the circulation: studies with poly(ethylene glycol)-coated vesicles. Biochim Biophys Acta 1062:77-82.

Sternberg, B. (1996). "Morphology of cationic liposome/DNA complexes in relation to their chemical composition." J Liposome Res 6: 515-533.

Templeton NS, Alspaugh E, Antelman D, Barber J, Csaky KG, Fang B, Frederik P, Honda H, Johnson D, Litvak F, Machemer T, Ramesh R, Robbins J, Roth JA, Sebastian M, Tritz R, Wen SF, Wu, Z (1999): Non-viral vectors for the treatment of disease. Keystone Symposia on Molecular and Cellular Biology of Gene Therapy, Salt Lake City, Utah.

Templeton, NS. (2001) Developments in liposomal gene delivery systems. Expert Opin. Biol. Ther. 1(4):1-4.

Templeton NS, Lasic DD (1999): New directions in liposome gene delivery. Molecular Biotechnology 11:175-180.

Templeton NS, Lasic DD, Frederik PM, Strey HH, Roberts DD, Pavlakis GN (1997): Improved DNA: liposome complexes for increased systemic delivery and gene expression. Nature Biotechnology 15:647-652.

Uziely B, Jeffers S, Isacson R, Kutsch K, Wei-Tsao D, Yehoshua Z, Libson E, Muggia FM, Gabizon A (1995): Liposomal doxorubicin: antitumor activity and unique toxicities during two complementary phase I studies. J Clin Oncol 13:1777-1785.

* cited by examiner

REVERSIBLE MASKING OF LIPOSOMAL COMPLEXES FOR TARGETED DELIVERY

CROSS REFERENCE TO RELATED APPLICATIONS

The present application, pursuant to 35 U.S.C. 111(b), claims the benefit of the filing date of provisional application Ser. No. 60/366,764 filed Mar. 22, 2002, and entitled "Reversible Masking of Liposomal Complexes for Targeted Delivery."

BACKGROUND OF THE INVENTION

1. Field of the Invention

The present invention relates to the targeted delivery of liposomal complexes. In particular, the present invention relates to the reversible masking of liposomal complexes to allow for the systemic circulation of liposomal complexes, the efficient delivery of a nucleic acid or drug product to target tissues, and bypass non-target tissues/organs.

2. Description of the Related Art

The primary goal of gene therapy is to introduce genetic material, or a gene, into a given set of cells to provide those cells with a new protein manufacturing capacity. Success is measured by how well the added gene functions to produce the therapeutic protein. Successful gene therapy must overcome a number of problems, one of which is delivering the gene to the correct destination.

A "vector" is defined as the means for carrying foreign genetic material into a cell. Gene therapy vectors can be placed into two broad categories; the viral vectors and the non-viral vectors.

Viral vectors comprise about 90% of the currently used means of gene delivery. In viral vectors, the gene is engineered into a modified virus in hopes of capitalizing on the infectivity of the virus. Briefly, essential viral genes are removed to render the virus incapable of replicating or, in some cases, restricting viral replication to the cell targeted by the therapy. A therapeutic gene or genes replace the viral genes that have been removed. Over long spans of viral and host evolution, viral vectors have refined a wide range of gene-packaging and cell-entry mechanisms. Through highly specific means, typically involving cell surface receptors, these modified viruses gain entrance to cells. In the cell, they are able to evade intracellular degradation and to induce the expression of the virally introduced therapeutic genes. The principal viral vectors used are retroviruses, adenoviruses, adeno-associated viruses and herpes viruses.

Despite the extensive use of viral vectors, there are a number of disadvantages associated with the use of viral vectors. These disadvantages include: 1) the generation of immune responses to expressed viral proteins that subsequently kill the target cells required to produce the therapeutic gene product; 2) the random integration of some viral vectors into the host chromosome; 3) the clearance of viral vectors delivered systemically; 4) the difficulties in engineering viral envelopes or capsids to achieve specific delivery to cells other than those with natural tropism for the virus; 5) the potential recombination of the viral vector with DNA sequences in the host chromosome to generate a replication-competent, infectious virus; 6) the inability to administer certain viral vectors more than once; 7) the high costs of producing large amounts of high-titer viral stocks for use in clinical trials; and 8) the limited size of the nucleic acid that can be packaged in viral vectors.

Tremendous effort has been devoted to the development of non-viral delivery systems because of the perceived problems involved in using viral vectors. There are numerous patents that have described nucleic acid-containing liposomes. For example, the following U.S. Patents describe the use of liposomes to deliver nucleic acids: U.S. Pat. Nos. 6,316,024; 6,284,267; 6,271,206; 6,217,901; 6,159,745; 6,096,716; 6,056,973; 5,958,791; 5,891,468; 5,858,784; 5,820,873; 5,776,487; 5,756,353; 5,718,915; 5,662,930; 5,614,214; and 5,552,157.

Negatively charged, or pH-sensitive liposomes can be used. These liposomes entrap DNA rather than complex with it. Since both the DNA and the lipids used are negatively charged, repulsion occurs, although some DNA is entrapped in the aqueous interior of these liposomes.

The vast majority of liposomes used are cationic liposomes. Some liposomes are capable of enveloping anionic plasmid DNA and can carry and deliver naked DNA into targeted cells. Positively charged liposomal complexes can bind to the negatively charged cell surface and either be incorporated into cell membranes, liberating their DNA content into the cytoplasm, or be internalized in an endosome where the liposomes are ruptured and their contents released into the lysosome fused with the endosome. Therefore, cell entry through the endocytic pathway leads to the bulk of the DNA being degraded and a small amount released into the cell cytoplasm.

Liposomes have traditionally been considered biologically inert and can be standardized and regulated as drugs rather than as biologics. The use of liposomes in gene therapy provides multiple advantages: 1) the lack of immunogenicity; 2) the lack of clearance by complement using improved formulations; 3) the unlimited size of nucleic acids that can be delivered (from single nucleotides to large mammalian artificial chromosomes); 4) the ability to perform repeated administrations in vivo without adverse consequences; 5) the relative ease and lower cost in creating nucleic acid-liposomal complexes in large quantities for clinical trials; 6) the relative ease in creating targeted complexes for delivery and gene expression in specific cell types, organs or tissues; and 7) the increased patient safety due to few or no viral sequences present in plasmids used to deliver therapeutic genes, thus precluding the theoretical risk of oncogenesis or super-infection associated with the potential generation of an infectious virus.

The traditional disadvantage of non-viral delivery systems has been the low levels of delivery and gene expression produced by liposomal complexes in targeted tissues. One major problem encountered has been the first-pass elimination of cationic liposomal complexes prior to distribution to the rest of the body. Liposomal complexes administered into the systemic circulation by any route, excluding the intraarterial, are subject to first-pass clearance in the lung prior to their distribution elsewhere. Thus, the lung serves as a temporary clearing site for a number of agents, especially cationic compounds.

There exists a need for a method to systemically administer cationic liposomal complexes that will avoid first-pass clearance by the lung.

SUMMARY OF THE INVENTION

The present invention relates to a masked, targeted liposomal complex for delivery of nucleic acid molecules and pharmaceuticals to cells or tissues, and a method for producing these masked, targeted liposomal complexes.

One aspect of the present invention is a liposomal complex for drug delivery, the liposomal complex comprising: a pharmaceutical surrounded and protected by a cationic lipid layer; and a masking agent reversibly associated with an exterior surface of the lipid layer, wherein the masking agent inhibits first-pass clearance of the liposomal complex by a lung tissue.

Another aspect of the present invention is a targeted liposomal complex comprising: a cationic liposome having an internal lipid bilayer and an external lipid bilayer; a pharmaceutical encapsulated between the internal lipid bilayer and the external lipid bilayer; a targeting ligand associated with an exterior surface of the external lipid bilayer of the cationic liposome; and a masking agent reversibly associated with the exterior surface of the external bilayer.

Yet another aspect of the present invention is a targeted liposomal complex comprising: a cationic bilamellar invaginated liposome comprising an extruded mixture of DOTAP and cholesterol; a plasmid encapsulated between an internal lipid bilayer and an external lipid bilayer of the liposome; a targeting ligand bound to an exterior surface of the cationic liposome; and a masking agent reversibly associated with the exterior surface of the liposome, wherein a concentration of the masking agent is decreases the zeta potential of the cationic liposome to less than 10 millivolts.

Still yet another aspect of the present invention is a process for optimizing the delivery of targeted liposomal complexes, the process comprising the steps of: selecting a reversibly interactive masking agent for a particular liposomal complex; titrating the liposomal complex with the masking agent to determine an amount of masking agent necessary to achieve a desired zeta potential; mixing the liposomal complex with the determined amount of the masking agent to form a masked liposomal complex; and testing the masked liposomal complex for delivery to a target tissue.

These and other objects, features and advantages of the present invention will become apparent with reference to the following description and drawing.

BRIEF DESCRIPTION OF THE DRAWINGS

For a more complete understanding of the present invention, and the advantages thereof, reference is now made to the following description taken in conjunction with the accompanying drawings, in which:

FIG. 1 is a graphical representation of a DNA:liposomal complex of the present invention.

FIG. 2 is a graphical representation of the delivery of nucleic acid molecules to distant tumor cells, not found in the lung, using masked and unmasked targeted liposomal complexes.

FIG. 3 is a graphical representation of the expression of chloramphenicol acetyltransferase (CAT) in MCF-7 breast cancer cells in the presence of increasing quantities of masking agent (in mM).

FIG. 4 is a graphical representation of the expression of chloramphenicol acetyltransferase (CAT) in mouse lung tissue with increasing quantities of masking agent associated with the liposomal complex surface (in mM).

FIG. 5 is a graphical representation of the expression of chloramphenicol acetyltransferase (CAT) in mouse heart tissue with increasing quantities of masking agent associated with the liposomal complex surface (in mM).

FIG. 6 is a graphical representation of the expression of CAT in the target tissue (i.e., the liver) in the presence or absence of a masking agent on the liposomal complex surface.

DESCRIPTION OF THE PREFERRED EMBODIMENTS

The present invention relates to a process for reversibly masking the positive charge of cationic liposomal complexes to allow the complexes to circulate throughout the body and inhibit first-pass clearance by the lung. Therefore, the present invention provides reversibly masked liposomal complexes with an improved ability to deliver their nucleic acid molecules or drug products to target tissues.

Delivery of nucleic acid-based therapeutics and pro-drugs or extremely toxic drugs to specific target tissues, organs or cells is desirable or required for certain applications. For example, lower amounts of liposomal complexes can be administered intravenously if the bulk of the injected material is delivered to target cells that are solely responsible for producing the therapeutic gene product, or metabolizing the pro-drug or toxic compound.

Injection of lower amounts of liposomal complexes is more cost-effective, safer for the patient, and more efficacious for the treatment of certain diseases. Furthermore, strategies such as most suicide gene approaches that are designed to kill target cells, such as tumor cells, require targeted delivery or the use of tissue specific gene promoters to express the suicide gene to avoid killing normal cells.

The standard approach to targeted delivery has been to coat the surface of the liposomal complexes with a cell or receptor specific ligand. Such liposomes, often referred to as "targeted liposomes", typically retain a substantial positive charge and have not been able to overcome the high first-pass elimination in the lung prior to distribution to the rest of the body. The uptake and expression of systemically administered DNA:liposomal complexes in various organs shows that the lung expresses the DNA delivered by the liposomal complex with at least a 10-fold higher efficiency than any other tissue (Templeton et al., 1997).

The present invention provides a process for reversibly masking the positive charge of cationic liposomal complexes, including targeted liposomal complexes. This masking process allows for the specific delivery of targeted liposomes to a specific tissue or cell type, when used with an appropriate ligand to bind and internalize through a specific cell surface receptor. The process of masking liposomal complexes includes the steps of selecting a reversibly associable masking agent for a particular targeted liposomal complex, titrating the liposomal complex with the masking agent to achieve a desired zeta potential, and testing the masked particle in vivo for its ability to pass through the lung and bind to the targeted organ.

Liposome Structure

Liposomes have different morphologies based upon their composition and the formulation method. Formulations frequently used for the delivery of nucleic acids are small unilamellar vesicles (SUVs), multilamellar vesicles (MLVs), or bilamellar invaginated structures (BIVs).

SUVs condense nucleic acids on the surface and form "spaghetti and meatballs" structures (Stemberg, 1996). DNA:liposomal complexes made using SUVs produce little or no gene expression upon systemic delivery, although these complexes transfect numerous cell types efficiently in vitro (Felgner et al., 1987; Felgner et al., 1994).

Complexes made using MLVs appear as "Swiss rolls" when viewing cross-sections by cryo-electron microscopy (Gustafsson et al., 1995). These complexes often become too large for systemic administration and are inefficient at delivering nucleic acids into cells due to MLVs inability to "unravel" at the cell surface. The addition of ligands onto the surface of an MLV DNA:liposomal complex further aggravates the problem of inefficient cell delivery. Therefore, MLVs are not particularly useful for the development of a model system for the targeted delivery of nucleic acids.

Figure 1:
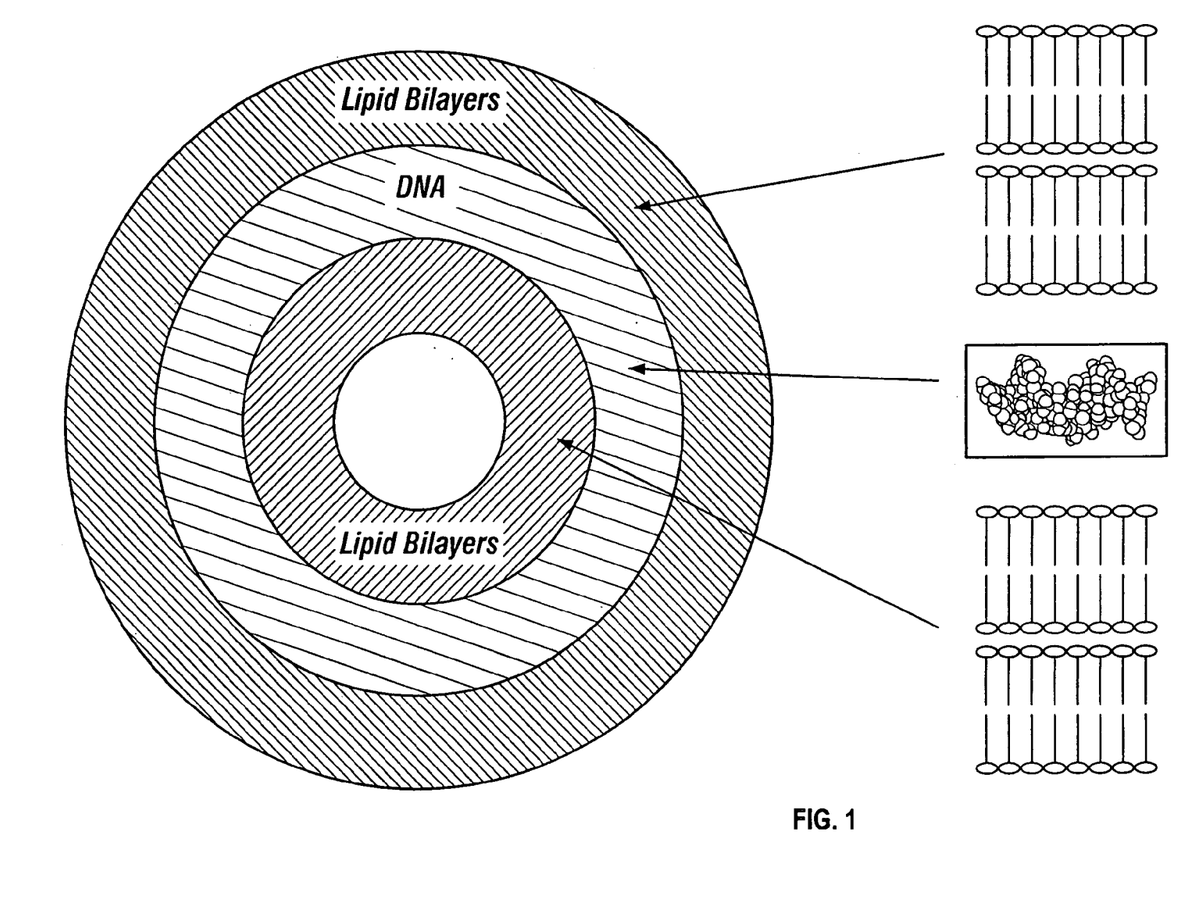

The preferred liposomal complexes are made with BIVs, or extruded DOTAP: Chol liposomes. As shown in FIG. 1, liposomal complexes made using BIVs efficiently encapsulate the nucleic acid between two bilamellar invaginated structures (Templeton et al., 1997). BIVs are created using DOTAP and cholesterol and a novel formulation procedure described in Templeton et al., 1997, which is hereby incorporated by reference. The formulation procedure is different because it includes a brief, low frequency sonication followed by manual extrusion of the liposomes through filters of decreasing pore size. The 0.1 and 0.2 mm filters are made of aluminum oxide rather than the polycarbonate used in other protocols. The aluminum oxide membranes contain more pores per surface area, the pores are evenly spaced and sized, and the pores have straight channels. During the manual extrusion process the liposomes are passed through each of four different sized filters only once.

BIVs condense unusually large amounts of nucleic acids of any size and the use of additional DNA condensing agents, including polymers, is unnecessary. For example, when plasmid DNA is condensed onto polymers prior to encapsulation in the BIVs, neither the incorporation of DNA into the liposomal complex nor the subsequent gene expression after transfection in vitro or in vivo was increased. Encapsulation of nucleic acids by these bilamellar invaginated structures alone is spontaneous and immediate, requiring only one step of simple mixing for sufficient encapsulation to occur. The extruded DOTAP: Chol-nucleic acid complexes are also large enough to avoid rapid clearance by Kupffer cells in the liver, and yet they will extravasate across tight barriers and diffuse through the target organ efficiently.

BIVs are effective at encapsulating many types of pharmaceuticals including pro-drugs, toxic drugs, viruses and nucleic acids. Although these preferred liposomes can be used for the effective delivery of a variety of compounds, the delivery of DNA or nucleic acids is used herein to exemplify the delivery system of the present invention.

Targeting Liposomes

Non-viral delivery vehicles have no target specificity, and therefore, re-targeting is not required. Targeting of liposomes is achieved by binding specific ligands to the exterior surface of liposomal complexes. Ligands are selected for their binding properties and their ability to be internalized through the specific cell surface receptors. Specific binding and delivery of a liposomal complex to a target cell is related to the specific binding of the ligand bound to the exterior surface of the liposomal complex to a surface protein, receptor, or some other specific factor located on the outside surface of the target cell. To efficiently bind a ligand to the surface of liposomal complexes, the nucleic acids or other pharmaceutical to be delivered are preferably encapsulated within the delivery vehicle before the addition of the ligand. Thus, the encapsulated nucleic acid or pharmaceutical does not prevent the attachment of the ligand on the surface of the liposomal complexes.

SUV liposomal: DNA complexes are difficult to target. The ligand is generally added to the SUV prior to mixing with DNA and probably interferes with the condensation of the DNA by the liposomes. Several investigators have reported that SUV liposomes-ligand conjugates condense nucleic acids inefficiently, as compared to liposomes alone. In addition, the nucleic acids are exposed on the surface of the liposomal complex and are not protected within the liposome.

In contrast, ligands can easily be bound onto the surface of the liposomal complexes formed with liposomes that encapsulate nucleic acids, such as BIVs. Monoclonal antibodies, Fab fragments, proteins, partial proteins, peptides, peptide mimetics, small molecules and drugs have been coated on the surface of BIV complexes after the encapsulation of the pharmaceutical within the liposomes (Templeton et al., 1997; Templeton and Lasic, 1999).

The addition of ligands to the surface of extruded BIV complexes does not significantly increase the mean particle size of the liposomal complex. Furthermore, extravasation and penetration through the target organ and gene expression produced after transfection are not diminished by the addition of ligands. These modified formulations are positively charged and deliver nucleic acids efficiently into cells in vitro and in vivo.

Attachment of Ligands

The most useful ligands for gene therapeutics in humans are those that are small, bind efficiently to the liposome, and possess a high affinity for target receptors and internalize the targeted complexes through the receptor. Although non-viral systems can be repeatedly administered without initiating an immune response, immune responses may be generated upon the repeated administration of liposomal complexes containing too much ligand or too large a ligand on the surface. These immune responses reduce the effectiveness and safety of the targeted liposomal complex.

Generally investigators attach the desired ligand to polyethyleneglycol (PEG) and use the PEG-ligand for incorporation into the liposomal structure, or for binding the ligand to the surface of the liposomal complexes.

Alternative strategies to the use of PEG include attachment of ligands through ionic interactions or by covalent attachment to "linker lipids". Negatively charged ligands can simply be adsorbed onto the surface of cationic liposomal complexes, such as BIVs. Additional moieties can be added to the ligand to increase the amount of negative charge without interfering with the ability of the modified ligand to efficiently bind to the appropriate cell surface receptor.

For example, succinylated asialofetuin has been used to target delivery of DNA:liposomal complexes to the asialoglycoprotein receptor on liver hepatocytes. The succinic acid amides increase the negative charge of the asialofetuin, and therefore, increase the binding of asialofetuin to the surface of liposomal complexes more efficiently than asialofetuin alone. The optimal amount of ligand to absorb onto the surface of the liposomal complexes is ligand dependent. Ultimately, in vivo transfection experiments must be performed to verify the optimal amount of ligand necessary to provide the highest level of delivery to the target cells and the highest levels of gene expression in these cells with little to no generation of an immune response.

Alternatively, ligands or modified ligands containing reactive groups can be covalently attached to linker lipids. These ligand-lipid conjugates must be checked for optimal activity of the ligand to bind to its receptor. Furthermore, the covalent linkage must not be immunogenic in animals or people after repeated administration. Ligand-lipid conjugates can be spontaneously inserted into the outside membrane of liposomal complexes in which the nucleic acids or pharmaceuticals are encapsulated within the liposomes. The amount of ligand-lipid used for insertion into the surface of complexes is also ligand dependent. Again, in vivo transfection experiments must be performed to verify the optimal amount of ligand-lipid needed to provide efficient delivery to the target cells and the highest levels of gene expression in these cells with little to no generation of an immune response.

Non-Specific Distribution of Liposomes

Cell surfaces are negatively charged, with specific cell types varying in their density of negative charge. These differences in charge density can influence the ability of cells to bind cationic liposomal complexes and are thought to contribute to the first-pass clearance and concentration of these liposomal complexes primarily in the lung. In addition, opsonization of liposomes with plasma proteins has been reported to enhance nonspecific clearance of liposomes from blood. For example, cationic DNA:SUV liposomal complexes have a short half-life within the circulation, generally about 5 to 10 minutes. Large molecular weight polyethylene glycol (PEG) and polyethylene glycol derivatives have been added to such liposome formulations to shield their positive charge and to extend the half-life of these liposomal complexes in the circulation. PEG is generally covalently linked to the liposomal complexes to provide increased liposomal complex stability (Papahadjopoulos et al., 1991; Senior et al., 1991; Gabizon et al., 1994). However, others have prepared large anionic PEG derivatives that interact with non-viral gene vectors by electrostatic interaction (Finsinger et al., 2000).

The PEGylated SUVs that have been described and used clinically have the DNA on the exterior surface of the lipid or liposome. The targeting ligand is most often attached to the DNA, rather than the lipid and the large negatively charged PEG molecules are thought to sterically hinder the binding of the targeting ligand to the target cell. Therefore, the few PEGylated SUVs with DNA on the interior must be purified prior to use in vitro or in vivo. Although the PEGylation of the SUVs extends the half-life of these liposomal complexes, it creates other problems that have not been solved.

One of these problems is that binding to the cell and efficient transfection of cells by cationic complexes is, in part, contributed by adequate charge interactions. For example, recent publications report that certain viruses have a partial positive charge around key subunits of viral proteins on the viral surface responsible for binding to cell surface receptors. Furthermore, this partial positive charge is required for virus entry into the cell through the receptor. Therefore, maintenance of adequate positive charge on the surface of targeted liposome complexes is essential for optimal delivery into the cell.

The PEGylation of SUVs significantly shields the positive charge on the SUV-complexes, thereby decreasing not only the non-specific uptake of the SUVs by the lung and heart but also the specific uptake of the SUVs by the targeted cells or tissue. The covalent attachment of PEG derivatives to the liposomal complexes are not reversible, even in the blood stream, and hinder delivery of cationic liposomes into cells due to steric hindrance and preclude ionic interactions between the cationic liposome and the negatively charged cell membrane.

Furthermore, the resulting extremely long half-life of the DNA:liposomal complex in the circulation (i.e. several days) has caused problems for patients. The PEGylation of SUVs has resulted in the non-specific accumulation of the bulk of the injected liposomal complexes in the skin, hands, and feet causing contract mucositis and Hand and Foot Syndrome (Gordon et al., 1995; Uziely et al., 1995) in patients and inducing extreme patient discomfort.

In general, PEGylation shields the positive charge on cationic complexes and is unable to "deshield" upon contact with the target cell surface. Therefore, the PEGylated complexes cannot utilize critical charge interactions for binding to target cells or for the optimal transfection of those cells. Furthermore, the PEGylated complexes are not fusogenic and must enter the cell through the endocytic pathway, leading to the degradation of most of the DNA in the few PEGylated complexes that do reach the target cells.

In contrast to the SUVs, BIV-nucleic acid complexes, with or without ligands, have a five-hour half-life in the circulation, and do not accumulate in the skin, hands or feet. Extended half-life in the circulation is provided primarily by the formulation, preparation method, injection of optimal colloidal suspensions, and optimal nucleic acid: lipid ratios used for mixing complexes, serum stability, and size (200–450 nm) (Templeton et al., 1997). Therefore, these bilamellar invaginated liposomes are the preferred embodiment for targeted non-viral delivery systems that require encapsulation of nucleic acids. The BIV liposomes have two lipid bilayers and encapsulate and protect the DNA or other pharmaceutical between the two lipid bilayers as shown in FIG. 1. The targeting ligand is bound to the outside surface of the outer lipid bilayer, thereby retaining a positive charge on the external surface of the DNA:liposomal complex.

In the present invention the masking agent interacts in a reversible manner with the positive charge on the external surface of the exterior lipid bilayer. Unlike the targeting ligand, the masking agent is reversibly associated with the liposomal complex. Thus, the masking agent has a higher dissociation rate from the outer lipid bilayer than the ligand.

Reversibly Masking the Liposomal Surface Charge

In the present invention, the process described herein as "masking" is used to describe the interaction of certain compounds with the outer surface of liposomal complexes to inhibit first-pass lung clearance and allow highly efficient binding of the liposomal complexes to target cells. The key to effective masking is to provide a masking agent that is reversibly associated with the liposomal complex so that once the first-pass clearance has been avoided; the liposomal complexes are still capable of binding to the target cells and delivering the therapeutic contents of those liposomal complexes across the cell membrane of the target cell in a highly efficient manner.

Selecting appropriate masking agents. The size of the masking agent will vary somewhat proportionately with the size of a targeting ligand and will generally be smaller than the targeting ligand. If the ligand is large (greater than or equal to about 10,000 daltons), such as an antibody molecule, the appropriate masking agent may be greater than or equal to about 5,000 daltons. If the ligand is medium sized (less than or equal to about 15,000 daltons), such as a small peptide, the appropriate masking agent is typically less than or equal to about 2,000 daltons. If the ligand is a small molecule or drug (less than or equal to about 5,000 daltons), the appropriate masking agent is typically less than or equal to about 500 daltons. The use of a large masking agent to mask a liposomal complex with a small targeting ligand attached to its surface, may prevent the ready dissociation of the masking agent from the liposomal surface. Since the effectiveness of the masking agent is dependent on the reversibility of its interaction with the liposomal surface, it is important to select the appropriate masking agent.

Masking agents are typically neutral lipids or other neutral or anionic compounds that are reversibly associated with the cationic liposomal complex surface. In contrast to prior PEGylated liposomal complexes currently available, the masking agent interacts with the liposomal complex with relatively weak bonds, such as hydrogen bonds or relatively weak ionic bonds. A masking agent must have a higher dissociation rate from the liposomal complex surface than the dissociation rate of a targeting ligand. In addition, a masking agent is not selected to interact with cell surfaces, but rather to temporarily mask the external positive charge on liposomal complexes to inhibit first pass clearance of the liposomal complex by the lung and other tissues due to non-specific binding. The masking agent must dissociate after by-pass of the lungs and non-target tissues, so that it can be delivered effectively to the target cells.

Since masking agents must undergo expensive, time-consuming in vivo experiments to verify that the masked liposome by-passes the lungs and other non-target tissues and is delivered to, and produces gene expression in, target tissues, preliminary in vitro experiments are run to assess the potential of a selected compound as a masking agent. An example of such a preliminary in vitro experiment is set out in Example 2.

Titrating the liposomal complex with the selected masking agent. Once a potential masking agent has been selected, the liposomal complex is titrated with that masking agent to determine the optimal concentration that will provide optimal delivery of the masked liposomal complex to the targeted tissue.

Experimental evidence has indicated that the zeta potential of the masked liposomal complexes can provide an indication of the appropriate masking agent concentration for the liposomal complex. The zeta potential is an important and useful indicator of the presence or absence of charged groups on the surface of particulates, i.e. liposomal complexes. It is reported in millivolts (mV) and is a measure of the overall charge of the suspension and an indicator of stability of a suspension wherein the greater the zeta potential, the more likely the suspension is to be stable because the charged particles repel one another and overcome the natural tendency to aggregate. For liposomal complexes in suspension, aggregation would be a disadvantage for delivery. Therefore, measurement of zeta potential is a tool that is used in the present invention in order to characterize liposomal complexes before and after masking.

In the process of producing the masked targeted liposomes of the present invention, the concentration of masking agent for interacting with the liposomal complexes is initially selected based on a desirable zeta potential. In the context of the present invention, a "desirable zeta potential" is one that is in the range of 4 to 16 mV and usually less than 10 mV. In a preferred embodiment, the masked liposomal complexes of the present invention have a zeta potential less than 10 mV.

For example, control cationic liposomes have a zeta potential of 60 to 70 mV. The BIV-DNA complexes of the present invention have a zeta potential of 45.5 mV when they were constructed without the addition of a masking agent. Addition of a masking agent to the BIV-DNA liposomal complex decreased the zeta potential of the BIV liposomal complexes indicating a masking of the positive charge on the surface of the liposomal complex. A variety of concentrations of the masking agent are added to the liposomal complexes and the zeta potential measured. It should be noted that some targeting ligands contribute negative charge to the liposomal complexes and will lessen the amount of masking agent needed to permit the liposomal complexes to bypass non-specific first-pass clearance in the lung.

The masked complexes having zeta potentials within the desirable range are then checked to see that they have not precipitated by measuring their O.D. 400. The mean particle size is also determined by dynamic light-scattering techniques to ensure that the liposomal complexes have not changed their size and are still 200–500 nm in mean particle size.

Figure 2:
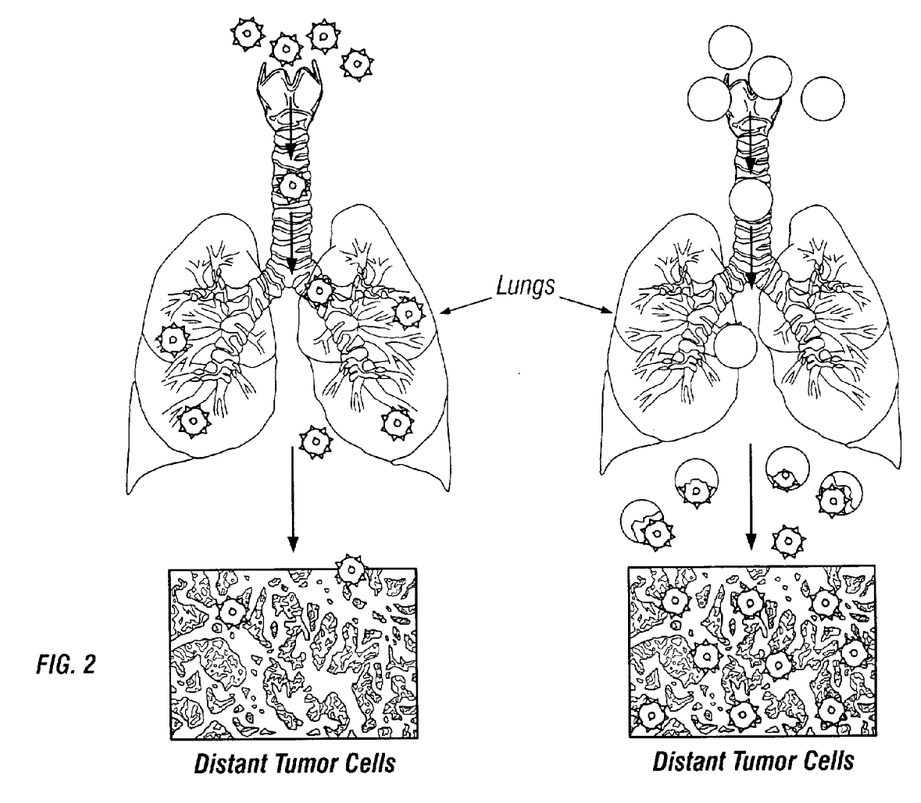

FIG. 2 depicts a graphical representation of the use of masked targeted liposomes of the present invention to target tumor cells in vivo and compares the results with use of non-masked targeted liposomal complexes. The unmasked targeted liposomal complexes, on the left hand side of FIG. 2, are represented as spheres with triangular spikes (the spheres represent the liposomal complex and the triangular spikes represent the ligand bound to the outer surface of the liposomal complex). As the unmasked targeted liposomal complexes pass through the lung, the majority of the liposomal complexes are taken up by the lung with only an occasional liposomal complex passing through the lung to be taken up by the distant tumor cells. The masked targeted liposomal complexes are shown on the right side of FIG. 2. The masked targeted liposomal complex is shown as a slightly larger sphere than the liposomal complex and is spikeless. The smooth sphere represents the outer layer of masking agent surrounding the liposomal complex. In contrast to the unmasked liposomal complex, the masked targeted liposomal complex passes through the lung without being taken up, or only minimally being taken up. As shown in FIG. 2, once the masked liposomal complex passes through the lung, the masking agent begins to disassociate from the targeted liposomal complex permitting it to be bound and taken up by the tumor cells.

The use of non-masked targeted liposomal complexes result in low levels of nucleic acid molecules delivered to the tumor cells due to clearance from the circulation in the lungs. In contrast, the masked targeted liposomal complexes significantly reduce the high levels of lung clearance and are delivered in much higher levels to the target cells. Clearly, the advantage of the masked targeted liposomes of the present invention is their reduced first-pass clearance in the lungs combined with their enhanced delivery to specific target tissues or cells and the subsequent high levels of gene expression in those target tissues or cells.

Gene Expression in Targeted Cells

Finally, in vivo transfection experiments are performed to verify the optimal amount of masking agent that will allow the liposomal complexes to pass through the lungs and be taken up and expressed in the target cell. These experiments involve the systemic administration of the masked targeted liposomal complexes, the harvesting of tissue and the measurement of the gene expression in the harvested tissue. The masked targeted liposomal complexes that have the highest gene expression in the targeted tissue are selected for clinical use.

EXAMPLE 1

Preparation of DNA:Liposomal Complexes

Preparation of Liposomes. BIV liposomes, specifically DOTAP: Chol liposomes, were used in the experimental protocols described below. The DOTAP: Chol liposomes were prepared as follows. The cationic lipid (e.g., DOTAP) was mixed with the neutral lipid cholesterol (Chol) at equimolar concentrations. Recently, synthetic cholesterol has been used to make clinical grade liposomal complexes. The optimal ration of DOTAP to synthetic cholesterol is 50:45, rather than 50:50. The mixed powdered lipids were dissolved in HPLC-grade chloroform. After the clear solution was rotated at 30° C. for 30 minutes to make a thin film, the film was dried under vacuum for 15 minutes. The film was hydrated in 5% dextrose in water to give a final concentration of 20 mM DOTAP and 20 mM Chol (or 18 mM for synthetic cholesterol), referred to as 20 mM DOTAP: Chol. The hydrated lipid film was rotated in a water bath at 50° C. for 45 minutes and then at 35° C. for 10 minutes. The mixture was allowed to stand in a covered flask at room temperature overnight, and then it was sonicated at low frequency for 5 minutes at 50° C., transferred to a tube, and heated for 10 minutes at 50° C. The mixture was sequentially extruded through Whatman (Kent, England) filters of decreasing size (1.0, 0.45, 0.2 and 0.1 micron) using syringes. The 0.2 and 0.1 micron filters used were Whatman ANOTOP. The prepared liposomes were stored under argon gas at 4° C.

DNA Preparation. The CAT plasmid used in these experiments was p4119 (Liu et al., 1995). For FIGS. 3–5, plasmid DNA was prepared using the QIAGEN ENDOFREE kit (Qiagen, Inc., Valencia, Calif.; Sigma Chemical Co., Inc., St. Louis, Mo.). For FIG. 6, the DNA was prepared using a variation of the alkaline lysis procedure of Maniatis (Smabrook, J. et al. 1989). The modifications included a 2 hour proteinase K digestion step immediately after RNase A digestion. Yields were in the range of 15 to 25 mg plasmid DNA per liter of bacterial culture.

Endotoxin levels of the plasmid DNA were 8 endotoxin units per microgram of DNA as determined using the chromogenic limulus amebocyte lysate assay (Kinetic-QCL; BioWhittaker, Walkersville, Md.). No genomic DNA, small DNA fragments, or RNA were detected in the DNA and the OD260/280 ratios of the plasmid DNA preparation were 2.0.

Preparation of DNA:Liposomal Complexes. Liposomal complexes were prepared the day before any planned in vitro or in vivo use. DNA was diluted in a solution of 5% dextrose in water. Equal volumes of the DNA solution and the liposome solution were mixed. Dilution and mixing were performed in 1.5 ml tubes with all reagents at room temperature. The DNA solution was added rapidly at the surface of the liposome solution. The DNA:liposome mixture was mixed rapidly up and down twice and then stored overnight at 4° C.

EXAMPLE 2

Identifying Potential Masking Agents

Masking agents will be neutral lipophilic compounds that will have an affinity for the liposomal lipid bilayers, or the masking agents will be weak anionic compounds that form ionic bonds with the cationic liposome. Once a potential masking agent has been selected, expensive time-consuming in vivo experiments must be performed to verify that the masked liposome by-passes the lungs and other non-target tissues and is delivered to and expressed in target tissues. Typically, the liposomal complex is titrated with varying concentrations of the selected masking agent to determine the optimal concentration of the masking agent that will provide optimal delivery of the masked liposomal complex to the targeted tissue in an animal model. The time and expense of such in vivo experiments generally dictate that preliminary in vitro tests be performed to select potential masking agents worthy of further pursuit.

Such preliminary in vitro tests include mixing varying concentrations of selected compounds with the liposomal complex immediately before incubating the masked liposomal complex with cells. Generally, potential masking agents are selected that will inhibit the transfection of the cells at concentrations less than 18 mM, preferably at less than 10 mM. Typically, potential masking agents will interact with the liposomal complex surface sufficiently to neutralize the positive charge of the liposomal complex and thereby decrease the uptake of the liposomal complex by cultured cells in vitro. However, the interaction of the masking agent with the liposomal complex must also be reversible when the liposomal complex is systemically administered in vivo.

A low molecular weight neutral lipid n-dodecyl-β-D-maltopyranoside, having a molecular weight of 510.6, was tested for its ability to mask non-specific binding of a cationic DNA:liposomal complex to MCF-7 breast cancer cells. CAT DNA:liposomal complexes were incubated with concentrations of n-dodecyl-β-D-maltopyranoside ranging from 4 mM to 18 mM immediately before mixing the masked liposomal complexes with the MCF-7 cells.

The MCF-7 cells were cultured in 6-well tissue culture clusters to 70% confluency. The cells were transfected with the CAT DNA:liposomal complexes, prepared as described in Example 1, using 5 μg of CAT plasmid DNA per well. Transfections were performed in serum-free medium for three hours. Six independent in vitro transfections were performed for each n-dodecyl-β-D-maltopyranoside concentration used. Enzyme-linked immunosorbent assays (ELISAs) were performed using the Roch (Indianapolis, Ind.) CAT ELISA kit. Three control wells of the MCF-7 cells were incubated with the liposomes alone to determine any background levels of cross-reactivity with the anti-CAT antibody. All CAT protein determinations were corrected for any CAT immunoreactivity detected in the control cells. Protein determinations were performed using the Micro BCA kit (Pierce, Rockford, Ill.).

Figure 3:
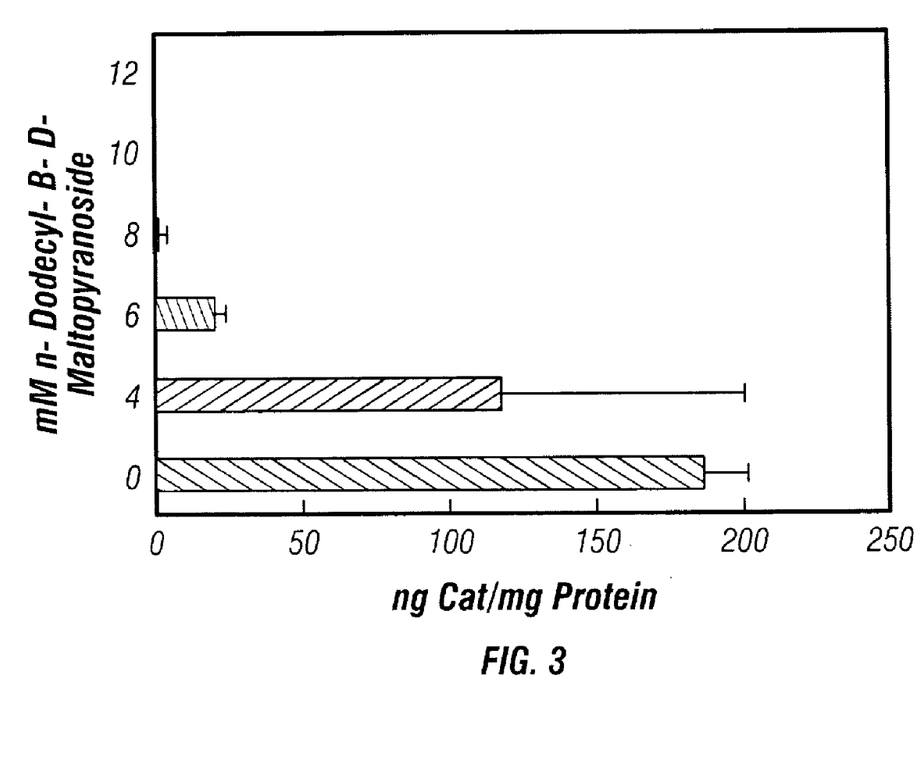

CAT production levels (ng CAT/ mg protein) for MCF-7 cells incubated with the various concentrations of n-dodecyl-β-D-maltopyranoside are shown in FIG. 3. The cells transfected with unmasked CAT DNA:liposomal complexes produced about 180 ng CAT/mg protein, while the cells transfected with CAT DNA:liposomal complexes masked with at least 8 mM n-dodecyl-β-D-maltopyranoside had negligible CAT production levels. Thus, n-dodecyl-β-D-maltopyranoside appears to be a strong candidate for a small molecular weight neutral lipid masking agent.

EXAMPLE 3

Adding Ligand to the DNA:Liposomal Complex

Once a potential masking agent is identified and ready to be tested in vivo, a ligand needs to be added to the DNA:liposomal complexes that will specifically bind to a particular cell type or tissue of interest. In the present example, succinylated asialofetuin was used to target delivery of the DNA:liposomal complexes to the asialoglycoprotein receptor on liver hepatocytes (Kaneo et al. 1991). The succinic acid amides increase the negative charge of the asialofetuin, and therefore, bound to the surface of liposomal complexes more efficiently than asialofetuin alone. The succinylated asialofetuin is bound to the liposomal complex surface via electrostatic interaction.

The DNA-liposomal complexes were filtered through a 0.45 μm polysulfone filter (Whatman) after mixing. Succinylated asialofetuin (0.2 mg/ml) was added to these filtered DNA:liposomal complexes using a Pipetman pipet tip. This mixture was mixed slowly up and down twice in the pipet tip. DNA:liposomal complexes were stored overnight at room temperature or about 25° C. No precipitation of the DNA:liposome-asialofetuin complexes occurred.

EXAMPLE 4

Masking the Liposomal Complexes

The masking agent used in this example was a PEG polymer. A pendant-modified PEG NHS ester having 5 pendant carboxyl groups added to a PEG polymer of molecular weight 5000 was selected. The pendant carboxyl groups were located along the backbone of the PEG chain.

Various concentrations, from 0.0004 mM to 16 mM, of the 5000 molecular weight PEG polymer were gently added to the liposomal complexes immediately before measuring the zeta potential of the masked liposome using a Delsa 440 SX Zeta Potential Analyzer (Beckman Coulter, Miami, Fla.). The addition of concentrations of the masking agent between about 4 mM and 16 mM resulted in liposomal complexes with zeta potentials less than 10 mV. With 4 mM masking agent added, the zeta potential was 9.8 mV. With the addition of 8 mM masking agent, the zeta potential was 6.5 mV, while with 16 mM masking agent, the zeta potential measured was as low as 4.8 mV. The masking agent is added to the complexes just prior to injections into animals by gentle mixing.

EXAMPLE 5

In Vivo Delivery and Gene Expression

Experiments were performed to demonstrate the specific targeting of the masked liposomes of the present invention by demonstrating their ability to avoid the first-pass clearance effect. Balb/c mice (each mouse was 6 weeks old and weighed about 20 gm) were injected into their tail veins with 200 μl of DOTAP: Chol:DNA complexes (4 mM DOTAP: Chol and 100 μg DNA) for the targeting experiments shown in FIG. 5. For experiments assessing non-targeted complexes (see FIGS. 3 and 4) mice were injected with 80 μl of liposomal complexes (4 mM DOTAP: Chol and 40 μg of Endotoxin-free DNA prepared using the Qiagen Endotoxin-Free Kit). The DNA inserted was a CAT reporter plasmid that if successfully transfected into cells would lead to expression of CAT in the target cells. The masking agent used on the liposome complexes was a 5000 MW PEG polymer with 5 pendant carboxyl groups. Masking agent levels were titrated to determine the optimal concentration for use at levels between 0.0004 mM and 16 mM (i.e., 0.0004, 0.004, 0.04, 0.4, 4, 8, 10, 12, 14 and 16 mM) as shown in FIGS. 4 and 5.

The mice were sacrificed 24 hours post-injection and the heart and lung were harvested and quickly frozen with liquid nitrogen. Tissues extracts were prepared and enzyme-linked immunosorbent assays (ELISAs) were performed using the Boehringer Mannheim (Indianapolis, Ind.) CAT Elisa kit to detect CAT immunoreactivity. All chloramphenicol acetyltransferase ("CAT") protein determinations were corrected for any CAT immunoreactivity detected in control tissues (i.e., the liposomes alone). Protein levels were determined using the Micro BCA kit (Pierce, Rockford, Ill.) and CAT production was reported as a function of total protein content of the tissue extract (ng CAT/mg protein).

The expression of the CAT gene delivered in masked DNA:liposomal complexes was determined in the lung and the heart. CAT expression in lung and heart tissues is shown in FIGS. 4 and 5 respectively. The first bar represents injection of the DNA:liposomal complexes with no targeting ligand or masking agent, while the other bars represent injections of the DNA:liposomal complexes coated with increasing concentrations of the masking agent (i.e., 0.0004 mM, 0.004 mM, 0.04 mM, 0.4 mM, 4 mM, 8 mM, 10 mM, 12 mM, 14 mM, and 16 mM of the PEG polymer described in Example 4). The error bars given in FIGS. 4 and 5 represent the standard deviation in experimental results from five mice.

Figure 4:
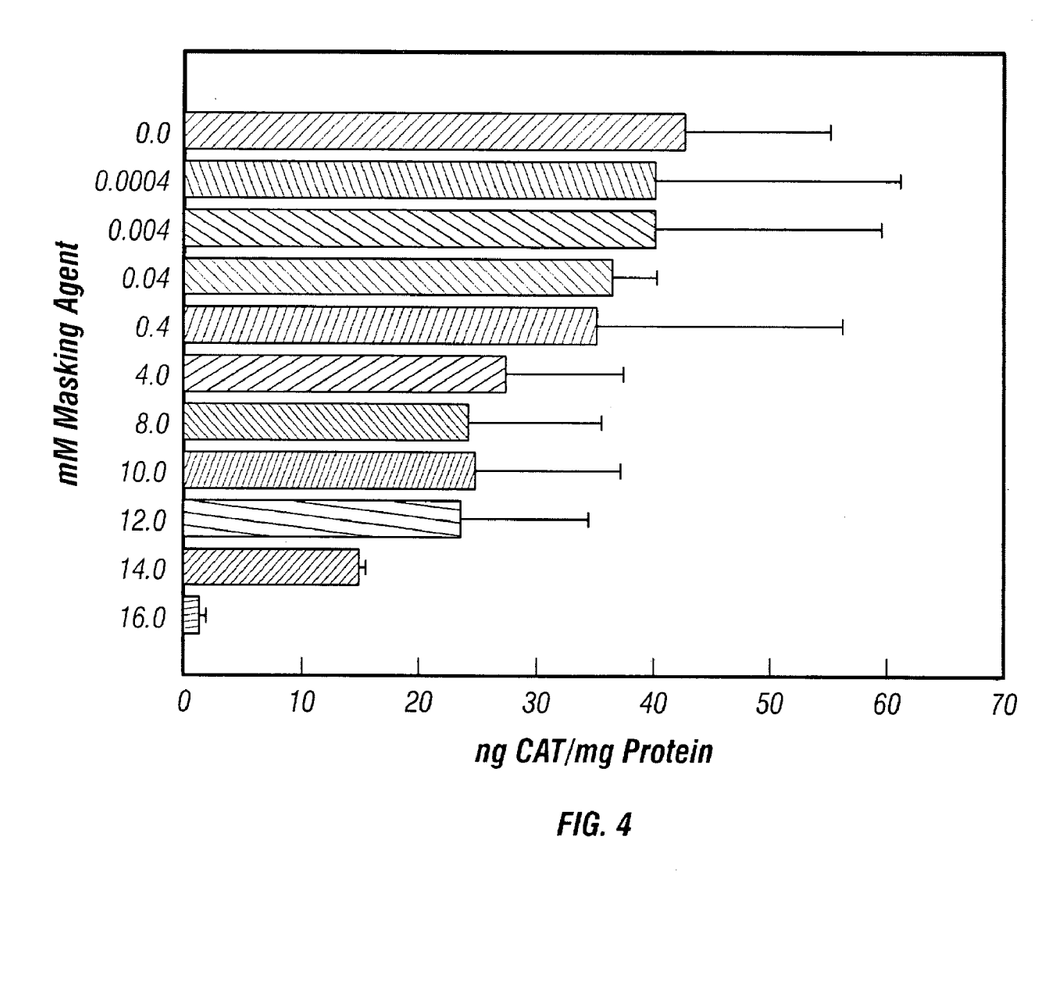
Figure 5:
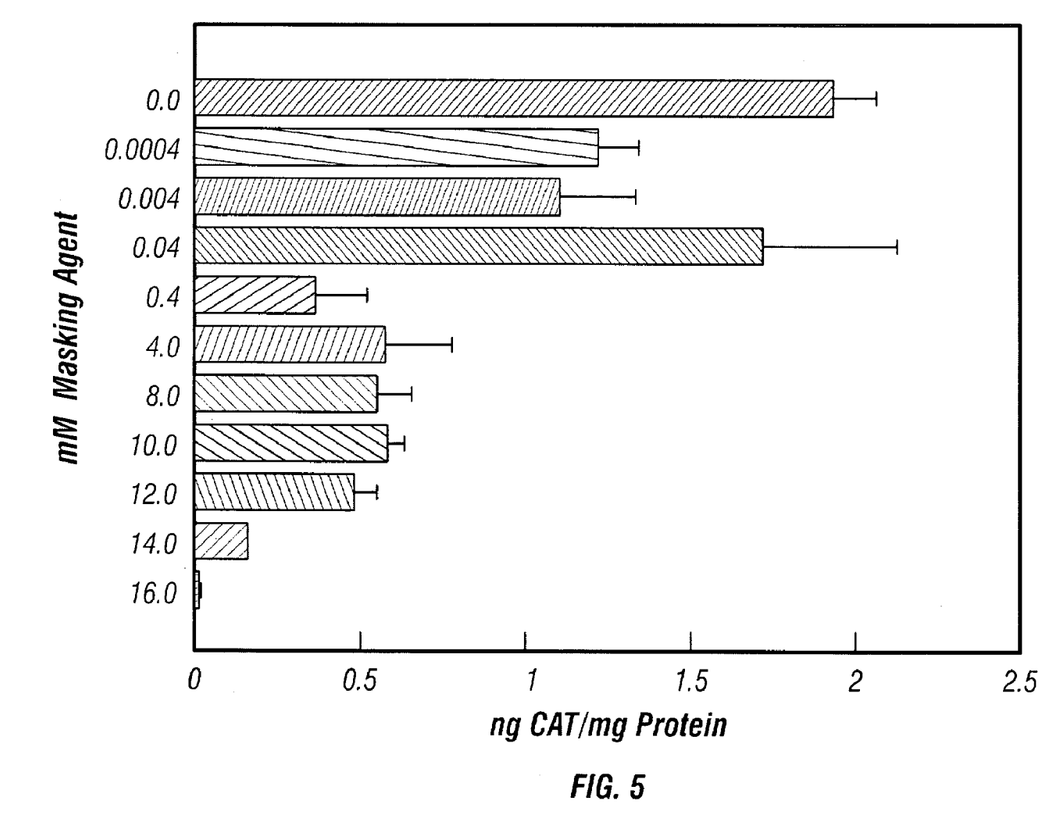

FIG. 4 shows the CAT expression in the lung. Injection of the liposomes alone gave a value of 0.05 ng CAT/mg protein in the lung, as compared to over 40 ng CAT/mg protein in the lung when the unmasked DNA:liposomal complexes were injected. Although the standard deviations in the CAT expression are large for the lower doses of masking agent, there is a general decrease in CAT expression with increased concentrations of masking agent. The injection of liposomal complexes masked with 16 mM PEG polymer resulted in 1 ng CAT/mg protein significantly lowering CAT expression in the lung.

FIG. 5 shows the CAT expression in the heart. Injection of the liposomes alone gave a value of 0.05 ng CAT/mg protein in the heart, as compared to almost 2 ng CAT/mg protein in the heart when the unmasked DNA:liposomal complexes were injected. Although, CAT expression in the heart never exceeds 2 ng CAT/mg protein, when the CAT: liposomal complexes are masked with 5000 PEG polymer the CAT expression is further reduced. Masking the liposomal complexes with 16 mM PEG polymer basically eliminates CAT expression in the heart.

Figure 6:
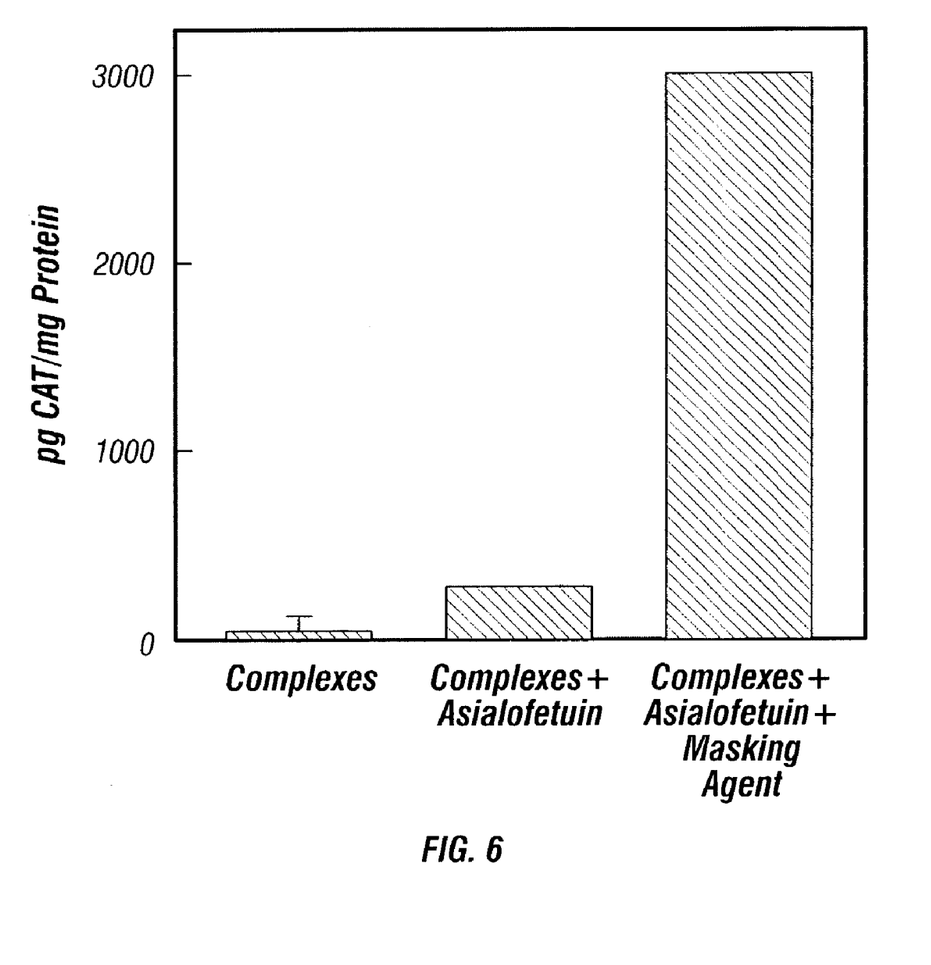

Additional experiments were performed to compare CAT expression in the liver with the injection of: DNA:liposomal complexes (unmasked and untargeted), targeted DNA:liposomal complexes (where succinylated asialofetuin was used as the targeting ligand), and the masked targeted DNA: liposomal complexes (where the 5000 molecular weight PEG polymer was used as the masking agent). Results of the experiments are shown in FIG. 6. Injected liposomal complexes resulted in extremely low levels of CAT expression in the liver (i.e., 40±1.14 S.E. pg CAT/mg protein). When the liposomal complexes had the targeting ligand succinylated asialofetuin on their outer surfaces, CAT expression in the liver showed a greater than six-fold increase (i.e., 275±14.1 S.E. pg CAT/mg protein). The succinylated asialofetuin contributed negative charge to the liposomal complexes, thereby reducing the concentration of 5000 dalton PEG polymer needed to mask the liposomal complexes. When the targeted liposomal complexes were reversibly masked with 10 mM 5000 molecular weight PEG polymer, an even higher expression of CAT in the liver was found (i.e., 3025±14.4 S.E. pg CAT/mg protein) or greater than a ten-fold increase of CAT expression over the targeted liposomal complexes. Each bar in FIG. 6 represents the mean and standard error values obtained from five mice.

The present invention is a masked, targeted liposomal complex that provides for specific and efficient delivery of nucleic acid molecules or pharmaceuticals to cells and tissues, both in vitro and in vivo. In one embodiment, the masked, targeted liposomal complexes are DOTAP:Chol:DNA complexes masked with a 5 pendant carboxyl group PEG 5000 dalton compound.

Other masking agents and liposomes are contemplated by the present invention and are chosen by one of skill in the art based on the masking agents' ability to produce efficient and specific delivery of liposomal complexes to target cells or tissues. Experiments would be performed as described above to titrate the amount and type of masking agent used, as well as, to test the efficiency of the targeting ligand. Such experiments are well within the ability of one of skill in the art.

The present invention is also a method for producing masked, targeted liposomes that comprises mixing a cationic lipid with a selected nucleic acid, virus, pro-drug, or other pharmaceutical to produce a cationic lipid-nucleic acid liposome complex that is targeted to cells or tissues in an animal, including humans, and masking a surface charge of the liposome complex immediately before use with an appropriate masking agent. The cationic lipid and anionic masking agent used are selected based on a desired zeta potential, and measurement of the level of translation of a transcribed nucleic acid that is produced in cells or tissues of animals, including humans. In the method of the present invention it is important to realize that the masking agent is added immediately before use of the liposomal complexes to ensure that it is bound loosely and does not interfere with the highly efficient binding and delivery of the liposomal complexes to their target tissues or cells. This represents one of the advantages of the present invention over current stealth technology where the PEG molecules allow for avoidance of first-pass clearance but do not allow for efficient target tissue binding and internalization. Therefore, the present invention provides a process for reversibly masking the positive charge of cationic liposomal complexes that includes the steps of selecting a reversibly associated masking agent for a particular liposomal complex, titrating the liposomal complex with the masking agent to achieve a desired zeta potential, and testing the masked particle in vivo for its ability to pass through the heart and lung, bind to the targeted organ or cells and internalize across the target cell membrane.

Although the present invention and its advantages have been described in detail, it should be understood that various changes, substitutions and alterations can be made herein without departing from the spirit and scope of the invention as defined by the appended claims. The examples described herein are exemplary only, and are not limiting. Many variations and modifications of the invention disclosed herein are possible and are within the scope of the invention.

REFERENCES

All patents and publications mentioned in this specification are indicative of the level of skill of those of knowledge in the art to which the invention pertains. All patents and publications referred to in this application are incorporated herein by reference to the same extent as if each was specifically indicated as being incorporated by reference and to the extent that they provide materials and methods not specifically shown.

Behr J-P, Demeneix B, Loeffler J P, Perez-Mutul, J (1989): Efficient gene transfer into mammalian primary endocrine cells with lipopolyamine-coated DNA. Proc Natl Acad Sci USA 86:6982–6986.

Felgner J H, Kumar R, Sridhar C N, Wheeler, C J, Tsai Y J, Border R, et al. (1994): Enhanced gene delivery and mechanism studies with a novel series of cationic lipid formulations. J Biol Chem 269:2550–2561.

Felgner P L, Gadek T R, Holm M, Roman R, Chan H W, Wenz M (1987): Lipofection: a highly efficient lipid-mediated DNA transfection procedure. Proc Natl Acad Sci USA 84:7413–7417.

Felgner P L, Ringold G M (1989): Cationic liposome-mediated transfection. Nature 337:387–388.

Finsinger D, Remy J-S, Erbacher P, Koch C, Plank C (2000): Protective copolymers by nonviral gene vectors: synthesis, vector characterization and application in gene delivery. Gene Therapy 7:1183–1192.

Gabizon A, Catane R, Uziely B, Kaufman B, Safra T, Cohen R, Martin F, Huang A., Barenholz Y (1994): Prolonged circulation time and enhanced accumulation in malignant exudates of doxorubicin encapsulated in polyethylene-glycol coated liposomes. Cancer Res 54:987–992.

Gordon K B, Tajuddin A, Guitart J, Kuzel T M, Eramo L R, VonRoenn, J (1995): Hand-foot syndrome associated with liposome-encapsulated doxorubicin therapy. Cancer 75:2169–2173.

Gustafsson J, Arvidson G, Karlsson G, Almgren, M (1995): Complexes between cationic liposomes and DNA visualized by cryo-TEM. Biochim Biophys Acta 1235:305–312.

Leventis R, Silvius J R (1990): Interactions of mammalian cells with lipid dispersions containing novel metabolizable cationic amphiphiles. Biochim Biophys Acta 1023:124–132.

Liu Y, Liggitt D, Zhong W, Guanhuan T, Gaensler K, Debs R (1995): Cationic liposome-mediated intravenous gene delivery. J Biol Chem 270:24864–24870.

Loeffler J P, Behr J-P (1993): Gene transfer into primary and established mammalian cell lines with lipopolyamine-coated DNA. Methods Enzymol 217:599–618.

Papahadjopoulos D, Allen T M, Gabizon A, Mayhew E, Matthay K, Huang S K, Lee K, Woodle M C, Lasic D D, Redemann C, Martin F J (1991): Sterically stabilized liposomes: improvements in pharmacokinetics and antitumor therapeutic efficacy. Proc Natl Acad Sci USA 88:11460–11464.

Pinnaduwage P, Huang L (1989): The role of protein-linked oligosaccharide in the bilayer stabilization activity of glycophorin A for dioleoylphosphatidylethanolamine liposomes. Biochim Biophys Acta 986:106–114.

Ramesh R, Saeki T, Templeton N S, Ji L, Stephens L C, Ito I, Wilson D R, Wu Z, Branch C D, Minna J D, Roth, J A (2001): Successful treatment of primary and disseminated human lung cancers by systemic delivery of tumor suppressor genes using an improved liposome vector. Molecular Therapy 3:337–350.

Rose J K, Buonocore L, Whitt M A (1991): A new cationic liposome reagent mediating nearly quantitative transfection of animal cells. Biotechniques 10:520–525.

Senior J, Delgado C, Fisher D, Tilcock C, Gregoriadis G (1991): Influence of surface hydrophilicity of liposomes on their interaction with plasma protein and clearance from the circulation: studies with poly(ethylene glycol)-coated vesicles. Biochim Biophys Acta 1062:77–82.

Stemberg, B. (1996). "Morphology of cationic liposome/DNA complexes in relation to their chemical composition." J Liposome Res 6: 515–533.

Templeton N S, Alspaugh E, Antelman D, Barber J, Csaky K G, Fang B, Frederik P, Honda H, Johnson D, Litvak F, Machemer T, Ramesh R, Robbins J, Roth J A, Sebastian M, Tritz R, Wen S F, Wu, Z (1999): Non-viral vectors for the treatment of disease. Keystone Symposia on Molecular and Cellular Biology of Gene Therapy, Salt Lake City, Utah.

Templeton N S, Lasic D D (1999): New directions in liposome gene delivery. Molecular Biotechnology 11:175–180.

Templeton N S, Lasic D D, Frederik P M, Strey H H, Roberts D D, Pavlakis G N (1997): Improved DNA:liposome complexes for increased systemic delivery and gene expression. Nature Biotechnology 15:647–652.

Uziely B, Jeffers S, Isacson R, Kutsch K, Wei-Tsao D, Yehoshua Z, Libson E, Muggia F M, Gabizon A (1995): Liposomal doxorubicin: antitumor activity and unique toxicities during two complementary phase I studies. J Clin Oncol 13:1777–1785.

What is claimed is:

1. A targeted liposomal complex comprising:
   a cationic liposome having an internal lipid bilayer and an external lipid bilayer;
   a pharmaceutical encapsulated between the internal lipid bilayer and the external lipid bilayer;
   a targeting ligand associated with an exterior surface of the external lipid bilayer of the cationic liposome; and
   a masking agent reversibly associated with the exterior surface of the external bilayer, wherein the masking agent is n-dodecyl-β-D-maltopyranoside.

2. The liposomal complex of claim 1, wherein a dissociation constant of the masking agent with the exterior surface of the lipid layer is greater than a dissociation constant of the targeting ligand with the exterior surface of the lipid layer.

3. The liposomal complex of claim 1, wherein the masking agent has a molecular weight that is less than a molecular weight of the targeting ligand.

4. The liposomal complex of claim 1, wherein the pharmaceutical includes a polynucleotide.

5. The liposomal complex of claim 1, wherein the pharmaceutical is a plasmid.

6. The liposomal complex of claim 1, wherein the pharmaceutical includes a peptide.

7. The liposomal complex of claim 1, wherein the cationic liposome has a pair of internal lipid bilayers and a pair of external lipid bilayers.

8. The liposomal complex of claim 1, wherein the cationic liposome is a bilamellar invaginated liposome comprising an extruded mixture of DOTAP and cholesterol.

9. The liposomal complex of claim 1, wherein the targeting ligand has a molecular weight ranging from about 500 daltons to about 5,000 daltons.

10. The liposomal complex of claim 1, wherein the concentration of the masking agent ranges from about 3 mM to about 10 mM.

11. A targeted liposomal complex comprising:
    a cationic liposome having an internal lipid bilayer and an external lipid bilayer;
    a pharmaceutical encapsulated between the internal lipid bilayer and the external lipid bilayer;
    a targeting ligand associated with an exterior surface of the external lipid bilayer of the cationic liposome; and
    a masking agent reversibly associated with the exterior surface of the external bilayer, wherein the masking agent is a pendant modified polyethylene glycol NHS ester having five pendant carboxyl groups located along the backbone of the polyethylene glycol chain and a molecular weight of about 5,000 daltons.

12. The liposomal complex of claim 11 having a zeta potential that is less than 16 millivolts.

13. The liposomal complex of claim 11 having a zeta potential ranging from about 3 millivolts to about 10 millivolts.

14. The liposomal complex of claim 11 having a mean particle size between about 200 nanometers and about 500 nanometers.

15. A liposomal complex for drug delivery, the liposomal complex comprising:
    a pharmaceutical surrounded and protected by a cationic lipid layer; and
    a masking agent consisting of n-dodecyl-β-D-maltopyranoside reversibly associated with an exterior surface of the lipid layer, wherein the masking agent inhibits first-pass clearance of the liposomal complex by a lung tissue.

16. The liposomal complex of claim 15, further comprising a targeting ligand associated with the exterior surface of the lipid layer.

17. The liposomal complex of claim 16, wherein a dissociation constant of the masking agent with the exterior surface of the lipid layer is greater than a dissociation constant of the targeting ligand with the exterior surface of the lipid layer.

18. The liposomal complex of claim 16, wherein the masking agent has a molecular weight that is less than a molecular weight of the targeting ligand.

19. The liposomal complex of claim 15 wherein the pharmaceutical includes a polynucleotide.

20. The liposomal complex of claim 19, wherein the pharmaceutical is a plasmid.

21. The liposomal complex of claim 15, wherein the pharmaceutical includes a peptide.

22. The liposomal complex of claim 15 having a zeta potential that is less than 16 millivolts.

23. The liposomal complex of claim 15 having a zeta potential ranging from about 3 millivolts to about 10 millivolts.

24. The liposomal complex of claim 15 having a mean particle size between about 200 nanometers and about 500 nanometers.

* * * * *